(12) United States Patent
Eckelbarger et al.

(10) Patent No.: US 8,835,409 B2
(45) Date of Patent: Sep. 16, 2014

(54) 3-ALKENYL-6-HALO-4-AMINOPICOLINATES AND THEIR USE AS HERBICIDES

(75) Inventors: Joseph D. Eckelbarger, Carmel, IN (US); Jeffrey B. Epp, Noblesville, IN (US); Paul R. Schmitzer, Indianapolis, IN (US); Thomas L. Siddall, Zionsville, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/356,722

(22) Filed: Jan. 24, 2012

(65) Prior Publication Data

US 2012/0190548 A1 Jul. 26, 2012

Related U.S. Application Data

(60) Provisional application No. 61/435,950, filed on Jan. 25, 2011.

(51) Int. Cl.
| | | |
|---|---|---|
| C07D 213/79 | (2006.01) | |
| C07F 7/08 | (2006.01) | |
| A01N 43/40 | (2006.01) | |
| A01N 55/00 | (2006.01) | |

(52) U.S. Cl.
CPC .......... *C07D 213/79* (2013.01); *C07F 7/0812* (2013.01); *A01N 43/40* (2013.01); *A01N 55/00* (2013.01)
USPC .............. 514/63; 514/75; 514/76; 514/79; 514/89; 514/183; 514/277; 514/352; 514/354; 504/193; 504/260; 504/320; 504/325; 546/14; 546/341; 546/345; 562/405; 562/493; 556/9; 556/12

(58) Field of Classification Search
USPC .......... 514/63, 75, 76, 79, 89, 183, 277, 352, 514/354; 546/2, 14, 22, 304, 310; 562/400, 562/405, 433, 456, 458
See application file for complete search history.

(56) References Cited

U.S. PATENT DOCUMENTS

| | | | |
|---|---|---|---|
| 6,297,197 B1 * | 10/2001 | Fields et al. ................. 504/260 |
| 8,536,331 B2 * | 9/2013 | Eckelbarger et al. ......... 544/329 |
| 2005/0032651 A1 * | 2/2005 | Balko et al. ................. 504/260 |
| 2010/0222221 A1 * | 9/2010 | Eckelbarger et al. ......... 504/239 |

* cited by examiner

*Primary Examiner* — Jane C Oswecki
(74) *Attorney, Agent, or Firm* — Michael R. Asam

(57) ABSTRACT

3-Alkenyl-6-halo-4-aminopicolinic acids and their derivatives are potent herbicides demonstrating a broad spectrum of weed control.

3 Claims, No Drawings

3-ALKENYL-6-HALO-4-AMINOPICOLINATES AND THEIR USE AS HERBICIDES

CROSS REFERENCE TO RELATED APPLICATIONS

This application claims the benefit of U.S. Provisional Patent Application Ser. No. 61/435,950 filed Jan. 25, 2011.

FIELD OF THE INVENTION

This invention relates to 6-halo-4-aminopicolinates and their derivatives and the use of these compounds as herbicides.

BACKGROUND OF THE INVENTION

A number of picolinic acids and their pesticide properties have been described in the art. U.S. Pat. Nos. 6,297,197, 6,784,137, and 7,314,849 disclose geneses of 6-aryl-4-aminopicolinic acids and their derivatives and their use as herbicides. Additionally, applications WO 2001/051468, WO 2003/011853, WO 2006/062979, US 2005/032651, WO 2007/082098, US 2004/0198608, US 2009/0088322, and WO 2011/144891 A1 disclose geneses of 6-substituted-4-aminopicolinic acids and their derivatives with halogen, cyano, thiocyanato, nitro, alkyl, haloalkyl, alkenyl, haloalkenyl, alkoxy, haloalkoxy, thioalkyl and aryloxy substituents in the 3-position and their use as herbicides.

SUMMARY OF THE INVENTION

It has now been found that certain 3-alkenyl-6-halo-4-aminopicolinic acids and their derivatives are superior herbicides with a broad spectrum of weed control against woody plants, grasses and sedges as well as broadleaves and with excellent crop selectivity. The compounds further possess excellent toxicological or environmental profiles.

Embodiments of the present invention include compounds of Formula I:

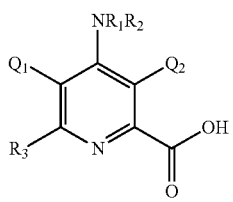

I wherein
$Q_1$ is selected from the group consisting of hydrogen and halogen;
$Q_2$ is selected from the group consisting of $C_1$-$C_4$ alkenyl, $C_1$-$C_4$ haloalkenyl, and $CXCYSi(R_4)_3$;
X is selected from the group consisting of hydrogen, fluorine, and chlorine;
Y is selected from the group consisting of hydrogen, fluorine, chlorine, $C_1$-$C_4$ alkyl, and $C_1$-$C_4$ haloalkyl;
$R_1$ and $R_2$ are independently selected from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;
$R_3$ is selected from the group consisting of the halogens; and
$R_4$ is selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_4$ groups can but need not be equivalent).

Embodiments of the invention also may include herbicidal compositions comprising a herbicidally effective amount of a compound of Formula I and agriculturally acceptable derivatives of the carboxylic acid group in a mixture with an agriculturally acceptable adjuvant or carrier. Embodiments of invention may also includes a method of use of the compounds and compositions of the present invention to kill or control undesirable vegetation by application of an herbicidal amount of the compound to the vegetation or to the locus of the vegetation as well as to the soil prior to emergence of the vegetation. The invention further includes intermediates for the preparation of the compounds.

DETAILED DESCRIPTION OF THE INVENTION

The herbicidal compounds of the present invention are derivatives of 4-aminopicolinic acids of Formula I:

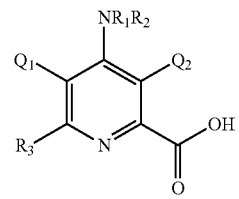

I wherein
$Q_1$ is selected from the group consisting of hydrogen and halogen;
$Q_2$ is selected from the group consisting of $C_1$-$C_4$ alkenyl, $C_1$-$C_4$ haloalkenyl, and $CXCYSi(R_4)_3$;
X is selected from the group consisting of hydrogen, fluorine, and chlorine;
Y is selected from the group consisting of hydrogen, fluorine, chlorine, $C_1$-$C_4$ alkyl, and $C_1$-$C_4$ haloalkyl;
$R_1$ and $R_2$ are independently selected from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;
$R_3$ is selected from the group consisting of the halogens; and
$R_4$ is selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy ($R_4$ groups can but need not be equivalent).

The carboxylic acids of Formula I can kill or control undesirable vegetation and are typically preferred. Analogs of these compounds in which the acid group of the picolinic acid is derivatized to form a related substituent that can be transformed within plants or the environment to an acid group possess essentially the same herbicidal effect and are within the scope of the invention. Therefore, an "agriculturally acceptable derivative," when used to describe the carboxylic acid functionality at the 2-position, is defined as any salt, solvate, hydrate, ester, acylhydrazide, imidate, thioimidate, amidine, amide, orthoester, acylcyanide, acyl halide, thioester, thionoester, dithioester, nitrile or any other acid derivative well known in the art which (a) does not substantially affect the herbicidal activity of the active ingredient, i.e., the 6-halo-4-aminopicolinic acid, and (b) is or can be hydrolyzed, oxidized or metabolized in plants or soil to the picolinic acid of Formula I that, depending upon the pH, is in the dissociated or the undissociated form. Agriculturally acceptable derivatives of the carboxylic acid may include agriculturally acceptable salts, esters and amides. Likewise, an "agriculturally acceptable derivative," when used to describe the amine functionality at the 4-position, is defined as any salt, solvate, hydrate, silylamine, phosphorylamino, phosphinimine, phosphoramidate, sulfonamide, sulfilimine, sulfoximine, aminal, hemiaminal, amide, thioamide, carbamate, thiocarbamate, amidine, urea, imine, nitro, nitroso, azide, or any other nitrogen-containing derivative well known in the art which (a) does not substantially affect the herbicidal activity of the active ingredient, i.e., the 6-halo-4-aminopicolinic acid, and (b) is or can be hydrolyzed in plants or soil to a free amine of Formula II. N-Oxides, which are also capable of breaking into the parent picoline of Formula II, are also covered by the scope of this invention.

Suitable salts may include those derived from alkali or alkaline earth metals and those derived from ammonia and amines. Preferred cations include sodium, potassium, magnesium, and aminium cations of the formula:

$R_5R_6R_7NH^+$ wherein $R_5$, $R_6$, and $R_7$ each, independently represents hydrogen or $C_1$-$C_{12}$ alkyl, $C_3$-$C_{12}$ alkenyl or $C_3$-$C_{12}$ alkynyl, each of which is optionally substituted by one or more hydroxy, $C_1$-$C_4$ alkoxy, $C_1$-$C_4$ alkylthio or phenyl groups, provided that $R_5$, $R_6$, and $R_7$ are sterically compatible. Additionally, any two of $R_5$, $R_6$, and $R_7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethanolamine, 2-methylthiopropylamine, bisallylamine, 2-butoxyethylamine, morpholine, cyclododecyl-amine, or benzylamine. Amine salts are often preferred forms of the compounds of Formula I because they are water-soluble and lend themselves to the preparation of desirable, aqueous-based herbicidal compositions.

Suitable esters may include those derived from $C_1$-$C_{12}$ alkyl, $C_3$-$C_{12}$ alkenyl or $C_3$-$C_{12}$ alkynyl alcohols, such as methanol, iso-propanol, butanol, 2-ethylhexanol, butoxyethanol, methoxypropanol, allyl alcohol, propargyl alcohol or cyclohexanol. Esters can be prepared by coupling of the picolinic acid with the alcohol using any number of suitable activating agents such as those used for peptide couplings such as dicyclohexylcarbodiimide (DCC) or carbonyl diimidazole (CDI), by reacting the corresponding acid chloride of a picolinic acid of Formula I with an appropriate alcohol or by reacting the corresponding picolinic acid of Formula I with an appropriate alcohol in the presence of an acid catalyst.

Suitable amides may include those derived from ammonia or from $C_1$-$C_{12}$ alkyl, $C_3$-$C_{12}$ alkenyl or $C_3$-$C_{12}$ alkynyl mono- or di-substituted amines, such as but not limited to dimethylamine, diethanolamine, 2-methylthiopropylamine, bisallylamine, 2-butoxyethylamine, cyclododecylamine, benzylamine or cyclic or aromatic amines with or without additional heteroatoms such as but not limited to aziridine, azetidine, pyrrolidine, pyrrole, imidazole, tetrazole or morpholine, unsubstituted or substituted. Amides can be prepared by reacting the corresponding picolinic acid chloride, mixed anhydride, or carboxylic ester of Formula I with ammonia or an appropriate amine.

The terms "alkyl," "alkenyl" and "alkynyl," as well as derivative terms such as "alkoxy," "acyl," "alkylthio" and "alkylsulfonyl," as used herein, include within their scope straight chain and branched chain moieties, unsubstituted or substituted. The terms "alkenyl" and "alkynyl" are intended to include one or more unsaturated bonds. The term "aryl," as well as derivative terms such as "aryloxy," refers to a phenyl.

Unless specifically limited otherwise, the term "halogen" including derivative terms such as "halo" refers to fluorine, chlorine, bromine, and iodine. The terms "haloalkyl" and "haloalkoxy" refer to alkyl and alkoxy groups substituted with from 1 to the maximum possible number of halogen atoms.

The compounds of Formula I can be made using well-known chemical procedures. The required starting materials are commercially available or readily synthesized utilizing standard procedures.

As shown in Scheme 1, picolinic esters of Formula I and Formula IV can be synthesized by reacting appropriately substituted 3-iodopicolinates of Formula II or Formula III with an organometallic compound ($Q_2$-M). In this case, M can be Sn ($R^8$)$_3$, where $R_8$ can be $C_1$-$C_{10}$ alkyl, or; M can be B(OR$_9$)(OR$_{10}$), where $R_9$ and $R_{10}$ are independent of one another and can be hydrogen, $C_1$-$C_6$ alkyl, or when taken together form an ethylene or propylene group; and "Catalyst" can be a transition metal catalyst, in particular a palladium catalyst such as bis(triphenylphosphine)palladium(II)dichloride.

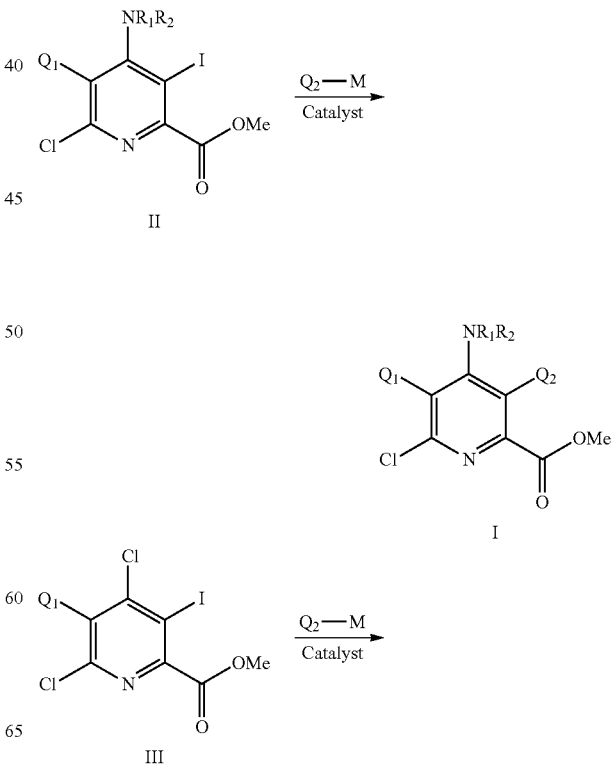

Scheme 1

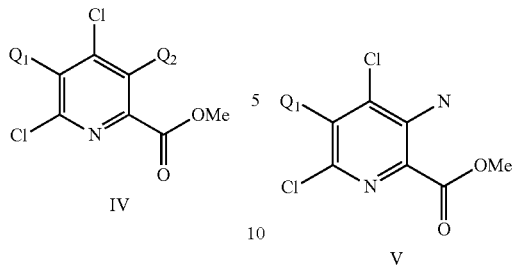

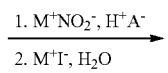

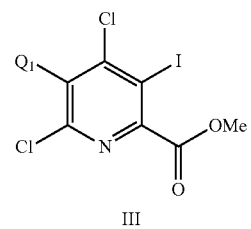

As shown in Scheme 2, 4-aminopicolinic esters of Formula I and Formula II can be synthesized by reacting appropriately substituted 4-chloropicolinate esters of Formula IV or Formula III with ammonia or primary or secondary amines in a polar solvent such as DMSO. Alternatively, the 4-amino ($R_1$=H, $R_2$=H) picolinic esters of Formula I and Formula II can be synthesized by reacting esters of Formula IV or Formula III with sodium or potassium azide and reduction of the intermediate azide with a reducing agent such as sodium borohydride.

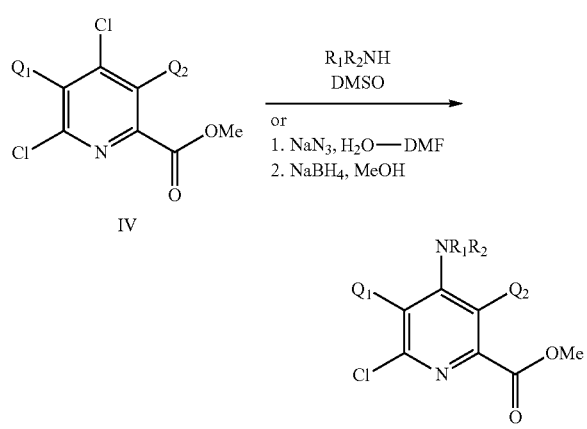

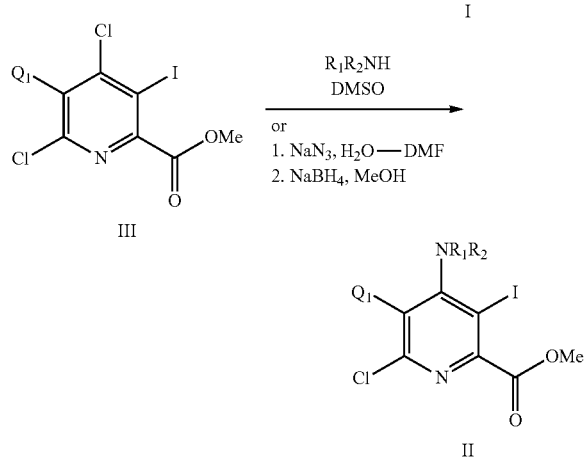

As shown in Scheme 3, the 4,6-dichloro-3-iodopicolinic esters of Formula III wherein $Q_1$ is hydrogen or chlorine can be synthesized from 3-amino-4,6-dichloropicolinic esters of Formula V by treatment with sodium or potassium nitrite in a strong mineral acid such as hydrochloric acid followed by reaction of the resultant diazonium salt with aqueous solutions of sodium or potassium iodide.

As shown in Scheme 4, 3-amino-4,6-dichloropicolinates of Formula V wherein $Q_1$ is hydrogen or chlorine can be synthesized from 3-aminopicolinates of Formula VI by treatment with a chlorinating agent such as N-chlorosuccinimide (NCS) in a polar solvent such as dimethyl formamide (DMF).

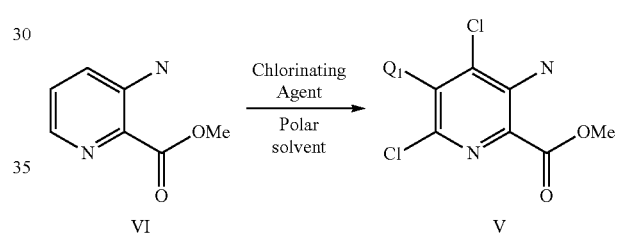

As shown in Scheme 5, 3-iodopicolinates of Formula II wherein $Q_1$ is fluorine can be synthesized from 5-fluoropicolinates of Formula VII by treatment with iodinating reagents such as periodic acid and iodine in a polar, protic solvent such as methyl alcohol at reflux temperature.

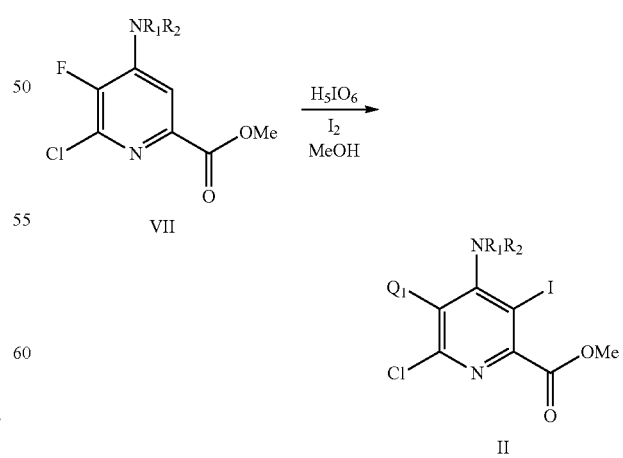

As shown in Scheme 6, 5-fluoropicolinates of Formula VII can be synthesized from 4,5,6-trichloropicolinates of Formula VIII. Accordingly, methyl 4,5,6-trichloropicolinate of Formula VIII can be converted to the corresponding isopropyl ester of Formula IX by reaction with isopropyl alcohol and concentrated sulfuric acid at reflux temperature under Dean-Stark conditions. The isopropyl ester of Formula IX can be reacted with a fluoride ion source such as cesium fluoride in a polar, aprotic solvent such as dimethyl sulfoxide under Dean-Stark conditions to yield the isopropyl 4,5,6-trifluoropicolinate of Formula X. The isopropyl 4,5,6-trifluoropicolinate of Formula X can be aminated with a amine such as ammonia in a polar, aprotic solvent such as dimethyl sulfoxide to produce 4-amino-5,6-difluoropicolinates of Formula XI. The fluorine substituent in the 6-position of 4-amino-5,6-difluoropicolinates of Formula XI can be exchanged with a chlorine substituent by treatment with a chloride source, such as hydrogen chloride in solvent such as dioxane to produce 4-amino-5-fluoro-6-chloropicolinates of Formula XII. Finally, 4-amino-5-fluoro-6-chloropicolinates of Formula XII can be transesterified to the corresponding methyl esters of Formula VII by reaction with titanium(IV) isopropoxide in methyl alcohol at reflux temperature.

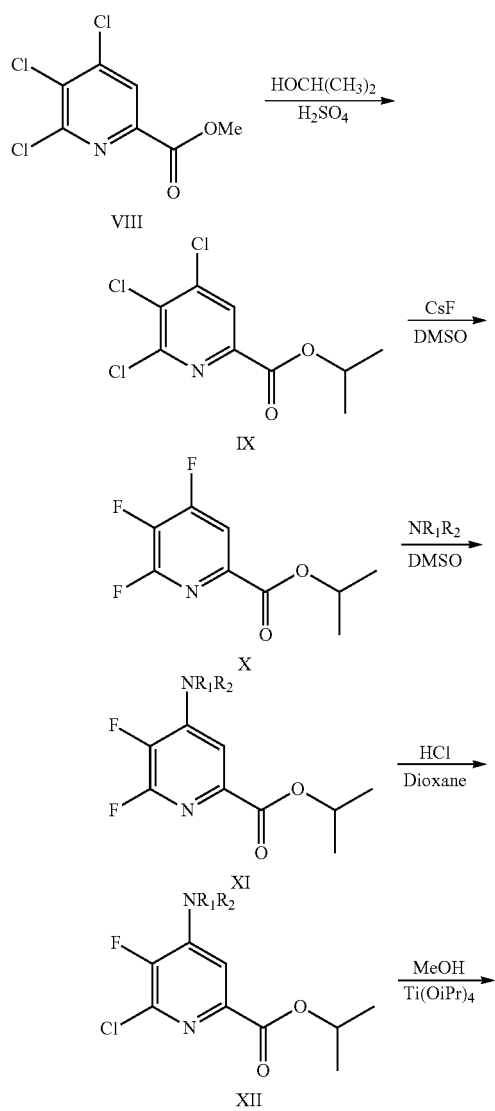

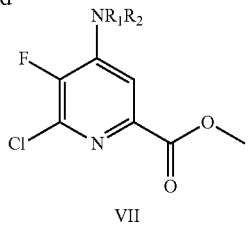

4-N-Amide, carbamate, urea, sulfonamide, silylamine and phosphoramidate amino derivatives can be prepared by the reaction of the free amino compound with, for example, a suitable acid halide, chloroformate, carbamyl chloride, sulfonyl chloride, silyl chloride or chlorophosphate.

The compounds of Formula I, obtained by any of these processes, can be recovered by conventional means. Typically, the reaction mixture is acidified with an aqueous acid, such as hydrochloric acid, and extracted with an organic solvent, such as ethyl acetate or methylene chloride. The organic solvent and other volatiles can be removed by distillation or evaporation to obtain the desired compound of Formula I, which can be purified by standard procedures, such as by recrystallization or chromatography.

The compounds of Formula I have been found to be useful as pre-emergence and post-emergence herbicides. They can be employed at non-selective (higher) rates of application to control a broad spectrum of the vegetation in an area or at lower rates of application for the selective control of undesirable vegetation. Areas of application include pasture and rangelands, roadsides and rights of way, power lines and any industrial areas where control of undesirable vegetation is desirable. Another use is the control of unwanted vegetation in crops such as corn, rice and cereals. They can also be used to control undesirable vegetation in tree crops such as citrus, apple, rubber, oil palm, forestry and others. The compounds may be employed postemergence. Furthermore, the compounds may be used to control a wide spectrum of woody plants, broadleaf and grass weeds, and sedges. Use of the compounds to control undesirable vegetation in established crops is permissible. While each of the compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinate seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I postemergence to relatively immature undesirable vegetation to achieve the maximum control of weeds.

Application rates of about 0.1 to about 1,000 g/Ha are generally employed in postemergence operations; for permanence applications, rates of about 1 to about 2,000 g/Ha are generally employed. The higher rates designated generally give non-selective control of a broad variety of undesirable vegetation. The lower rates typically give selective control and can be employed in the locus of crops.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: 4-CPA; 4-CPB; 4-CPP; 2,4-D; 3,4-DA; 2,4-DB; 3,4-DB; 2,4-DEB; 2,4-DEP; 3,4-DP; 2,3,6-TBA; 2,4,5-T; 2,4,5-TB; acetochlor, acifluorfen, aclonifen, acrolein, alachlor, allidochlor, alloxydim, allyl alcohol, alorac, ametridione, ametryn, amibuzin, amicarbazone, amidosulfuron, aminocyclopyrachlor, aminopyralid, amiprofos-methyl, amitrole, ammonium sulfamate, anilofos, anisuron, asulam, atraton, atrazine, azafenidin, azimsulfuron, aziprotryne, barban, BCPC, beflubutamid, benazolin, bencarbazone, benfluralin, benfuresate, bensulfuron, bensulide, bentazone, benzadox, benzfendizone, benzipram, benzobicyclon, benzofenap, benzofluor, benzoylprop, benzthiazuron, bicyclopyrone, bifenox, bilanafos, bispyribac, borax, bromacil, bromobonil, bromobutide, bromofenoxim, bromoxynil, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole chlorprocarb, carfentrazone, CDEA, CEPC, chlomethoxyfen, chloramben, chloranocryl, chlorazifop, chlorazine, chlorbromuron, chlorbufam, chloreturon, chlorfenac, chlorfenprop, chlorflurazole, chlorflurenol, chloridazon, chlorimuron, chlornitrofen, chloropon, chlorotoluron, chloroxuron, chloroxynil, chlorpropham, chlorsulfuron, chlorthal, chlorthiamid, cinidon-ethyl, cinmethylin, cinosulfuron, cisanilide, clethodim, cliodinate, clodinafop, clofop, clomazone, clomeprop, cloprop, cloproxydim, clopyralid, cloransulam, CMA, copper sulfate, CPMF, CPPC, credazine, cresol, cumyluron, cyanatryn, cyanazine, cycloate, cyclosulfamuron, cycloxydim, cycluron, cyhalofop, cyperquat, cyprazine, cyprazole, cypromid, daimuron, dalapon, dazomet, delachlor, desmedipham, desmetryn, di-allate, dicamba, dichlobenil, dichloralurea, dichlormate, dichlorprop, dichlorprop-P, diclofop, diclosulam, diethamquat, diethatyl, difenopenten, difenoxuron, difenzoquat, diflufenican, diflufenzopyr, dimefuron, dimepiperate, dimethachlor, dimethametryn, dimethenamid, dimethenamid-P, dimexano, dimidazon, dinitramine, dinofenate, dinoprop, dinosam, dinoseb, dinoterb, diphenamid, dipropetryn, diquat, disul, dithiopyr, diuron, DMPA, DNOC, DSMA, EBEP, eglinazine, endothal, epronaz, EPTC, erbon, esprocarb, ethalfluralin, ethametsulfuron, ethidimuron, ethiolate, ethofumesate, ethoxyfen, ethoxysulfuron, etinofen, etnipromid, etobenzanid, EXD, fenasulam, fenoprop, fenoxaprop, fenoxaprop-P, fenoxasulfone, fenteracol, fenthiaprop, fentrazamide, fenuron, ferrous sulfate, flamprop, flamprop-M, flazasulfuron, florasulam, fluazifop, fluazifop-P, fluazolate, flucarbazone, flucetosulfuron, fluchloralin, flufenacet, flufenican, flufenpyr, flumetsulam, flumezin, flumiclorac, flumioxazin, flumipropyn, fluometuron, fluorodifen, fluoroglycofen, fluoromidine, fluoronitrofen, fluothiuron, flupoxam, flupropacil, flupropanate, flupyrsulfuron, fluridone, fluorochloridone, fluoroxypyr, flurtamone, fluthiacet, fomesafen, foramsulfuron, fosamine, furyloxyfen, glufosinate, glufosinate-P, glyphosate, halosafen, halosulfuron, haloxydine, haloxyfop, haloxyfop-P, hexachloroacetone, hexaflurate, hexazinone, imazamethabenz, imazamox, imazapic, imazapyr, imazaquin, imazethapyr, imazosulfuron, indanofan, indaziflam, iodobonil, iodomethane, iodosulfuron, ioxynil, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-thioethyl, MCPB, mecoprop, mecoprop-P, medinoterb, mefenacet, mefluidide, mesoprazine, mesosulfuron, mesotrione, metam, metamifop, metamitron, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metobromuron, metolachlor, metosulam, metoxuron, metribuzin, metsulfuron, molinate, monalide, monisouron, monochloroacetic acid, monolinuron, monuron, morfamquat, MSMA, naproanilide, napropamide, naptalam, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxasulfuron, oxaziclomefone, oxyfluorfen, parafluoron, paraquat, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picolinafen, pinoxaden, piperophos, potassium arsenite, potassium azide, potassium cyanate, pretilachlor, primisulfuron, procyazine, prodiamine, profluazol, profluralin, profoxydim, proglinazine, prometon, prometryn, propachlor, propanil, propaquizafop, propazine, propham, propisochlor, propoxycarbazone, propyrisulfuron, propyzamide, prosulfalin, prosulfocarb, prosulfuron, proxan, prynachlor, pydanon, pyraclonil, pyraflufen, pyrasulfotole, pyrazolynate, pyrazosulfuron, pyrazoxyfen, pyribenzoxim, pyributicarb, pyriclor, pyridafol, pyridate, pyriftalid, pyriminobac, pyrimisulfan, pyrithiobac, pyroxasulfone, pyroxsulam, quinclorac, quinmerac, quinoclamine, quinonamid, quizalofop, quizalofop-P, rhodethanil, rimsulfuron, saflufenacil, S-metolachlor, sebuthylazine, secbumeton, sethoxydim, siduron, simazine, simeton, simetryn, SMA, sodium arsenite, sodium azide, sodium chlorate, sulcotrione, sulfallate, sulfentrazone, sulfometuron, sulfosulfuron, sulfuric acid, sulglycapin, swep, TCA, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone-methyl, thifensulfuron, thiobencarb, tiocarbazil, tioclorim, topramezone, tralkoxydim, tri-allate, triasulfuron, triaziflam, tribenuron, tricamba, triclopyr, tridiphane, trietazine, trifloxysulfuron, trifluralin, triflusulfuron, trifop, trifopsime, trihydroxytriazine, trimeturon, tripropindan, tritac, tritosulfuron, vernolate, and xylachlor.

The herbicidal compounds of the present invention can, further, be used in conjunction with glyphosate, glufosinate or 2,4-D on glyphosate-tolerant, glufosinate-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are acetolactate synthase inhibitors in sensitive plants can be treated. Many glyphosate- and glufosinate-tolerant crops can be treated as well, alone or in combination with these herbicides. Some crops (e.g. cotton) have been made tolerant to auxinic herbicides such as 2,4-dichlorophenoxyacetic acid. These herbicides may be used to treat such resistant crops or other auxin-tolerant crops.

While it is possible to utilize the compounds of Formula I directly as herbicides, it is preferable to use them in mixtures containing a herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophillite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl)sulfosuccinate; sorbitol esters, such as sorbitol oleate; quaternary amines, such as lauryl trimethylammonium chloride; polyethylene glycol esters of fatty acids, such as poly-ethylene glycol stearate; block copolymers of ethylene oxide and propylene oxide; and salts of mono- and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following examples are presented to illustrate the various aspects of this invention and should not be construed as limitations to the claims. Many of the starting materials useful for the preparation of the compounds of the present invention, e.g., methyl 3-aminopyridine-2-carboxylate are available from commercial sources.

EXAMPLES

General Considerations: Fluorine spectra were acquired at 376 MHz on a Bruker DRX400 spectrometer. The spectra were referenced to trichlorofluoromethane ($CFCl_3$) as an external standard and were typically conducted with proton decoupling.

Example 1

Preparation of methyl 3-amino-4,5,6-trichloropicolinate

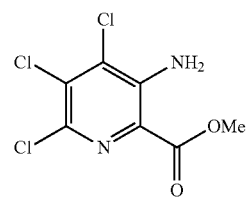 [SMILES: COC(=O)c1nc(Cl)c(Cl)c(Cl)c1N]

N-chlorosuccinimide (3.5 g, 26 mmol) and methyl 3-aminopicolinate (1.0 g, 6.6 mmol) were combined in dry DMF (20 mL) and stirred overnight at room temperature. The reaction mixture was poured into water (50 mL) and extracted twice with ethyl acetate. The combined organic extracts were washed with water, washed with saturated sodium chloride, dried over sodium sulfate, and concentrated under vacuum. The residue was chromatographed via reverse-phase HPLC (water/acetonitrile) to give the title compound as a white solid (0.93 g, 55%): mp 151-152° C.; $^1$H NMR (400 MHz, CDCl$_3$) δ 6.43 (s, 2H), 3.97 (s, 3H); EIMS m/z 254.

Example 2

Preparation of methyl 4,5,6-trichloro-3-iodopicolinate

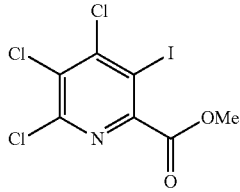 [SMILES: COC(=O)c1nc(Cl)c(Cl)c(Cl)c1I]

Methyl 3-amino-4,5,6-trichloropicolinate (0.5 g, 2.0 mmol) was dissolved in concentrated HCl (20 mL), cooled to 5° C., and treated with a solution of sodium nitrite (0.2 g, 3.0 mmol dissolved in 1 mL of water) over 15 minutes. The reaction mixture was stirred for 20 minutes at 5° C. and poured carefully into a rapidly stirred mixture of sodium iodide (1.8 g; 12 mmol) in water (100 mL) and dichloromethane (30 mL). After 20 minutes, solid sodium bisulfite was added. Ethyl acetate (100 mL) was added and the phases were separated. The organic phase was washed with saturated sodium chloride, dried over sodium sulfate, and concentrated under vacuum. The above procedure was performed again on 1.5 g of the amine and the combined crude products were purified by flash chromatography (SiO$_2$, hexane/ethyl acetate) to afford the title compound as a white solid (1.8 g 61%): mp 61-62° C.; $^1$H NMR (400 MHz, CDCl$_3$) δ 4.00 (s, 3H); EIMS m/z 365.

Example 3

Preparation of methyl 4-amino-5,6-dichloro-3-iodopicolinate

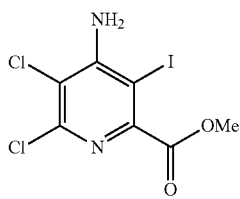 [SMILES: COC(=O)c1nc(Cl)c(Cl)c(N)c1I]

Methyl 4,5,6-trichloro-3-iodopicolinate (1.5 g, 4.1 mmol) was dissolved in dry dimethylsulfoxide (15 mL) and a slow stream of ammonia gas was bubbled through the solution as the temperature was raised to 70° C. The ammonia gas was bubbled through the heated solution for another 7 hours. The cooled reaction mixture was partitioned between ethyl acetate and water. The organic phase was washed with water, washed with saturated sodium chloride, dried over sodium sulfate, and concentrated under vacuum. The crude product was purified by flash chromatography (SiO$_2$, ethyl acetate/methylene chloride) to afford the title compound as a white solid (0.80 g, 56%): mp 122-23° C.; $^1$H NMR (400 MHz, CDCl$_3$) δ 5.57 (s, 2H), 3.97 (s, 3H); EIMS m/z 346.

Example 4

Preparation of methyl 4-amino-5,6-dichloro-3-vinylpicolinate (Compound 1)

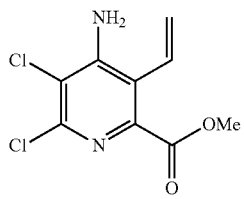

Methyl 4-amino-5,6-dichloro-3-iodopicolinate (0.5 g, 1.4 mmol), vinyltributylstannane (530 μl, 0.57 mmol, 1.8 mmol), and bis(triphenylphosphine)palladium(II) chloride (0.10 g, 0.1 mmol) were combined in nitrogen-deaerated 1,2-dichloroethane (10 mL). The reaction mixture was heated at reflux for 8 hours. The cooled reaction mixture was diluted with ethyl acetate (30 mL) and stirred with 15% KHF$_2$ solution (10 mL) for 30 minutes. The phases were separated and the aqueous phase was extracted with ethyl acetate. The combined organic phases were washed with saturated sodium chloride, dried over sodium sulfate, and concentrated under vacuum. The crude product was purified by flash chromatography (SiO$_2$, ethyl acetate/hexane) to afford the title compound as a tan solid (0.26 g, 73%): mp 96-97° C.; $^1$H NMR (400 MHz, CDCl$_3$) δ 6.85 (dd, J=18.1, 11.5 Hz, 1H), 5.72 (dd, J=11.5, 1.3 Hz, 1H), 5.53 (dd, J=18.1, 1.3 Hz, 1H), 5.19 (s, 2H), 3.91 (s, 3H); EIMS m/z 246 ([M−H]$^−$).

Compound 2 in Table 1 was synthesized as in Example 4.

Example 5

Preparation of methyl 3-amino-4,6-dichloropicolinate

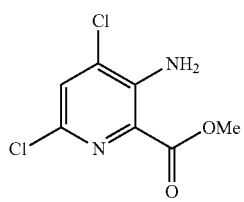 [SMILES: COC(=O)c1nc(Cl)cc(Cl)c1N]

N-chlorosuccinimide (0.88 g, 6.6 mmol) and methyl 3-aminopicolinate (0.5 g, 3.3 mmol) were combined in dry DMF (15 mL) and stirred overnight. The reaction mixture was poured into water (50 ml) and extracted twice with ethyl acetate. The combined organic extracts were washed again with water, washed with saturated sodium chloride, dried over sodium sulfate, and concentrated under vacuum. The crude product was purified by reverse-phase HPLC (water/acetonitrile) to give the title compound as a white solid (0.40 g, 55%): mp 127-128° C.; $^1$H NMR (400 MHz, CDCl$_3$) δ 7.42 (s, 1H), 6.33 (s, 2H), 3.97 (s, 3H); EIMS m/z 220.

Example 6

Preparation of methyl 4,6-dichloro-3-iodopicolinate

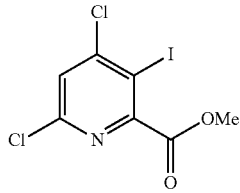 [SMILES: COC(=O)c1nc(Cl)cc(Cl)c1I]

Methyl 3-amino-4,6-dichloropicolinate (1.2 g, 5.4 mmol) was dissolved in concentrated HCl (15 mL), cooled to 5° C., and treated with a solution of sodium nitrite (0.56 g, 8.1 mmol) in 2 ml of water. The reaction mixture was stirred for 20 minutes at 5° C. and then poured carefully into a rapidly stirred mixture of sodium iodide (3.8 g; 25 mmol) in 30 mL water and 30 mL of dichlormethane. After 30 minutes, a dilute solution of sodium bisulfite was added. The dichloromethane phase was separated and washed with water, washed with saturated sodium chloride, dried over sodium sulfate, and concentrated under vacuum. The crude product was purified by flash chromatography (SiO$_2$, hexane/ethyl acetate) to give the title compound as a tan solid (0.60 g, 33%): 82-83° C.; $^1$H NMR (400 MHz, CDCl$_3$) δ 7.53 (s, 1H), 4.00 (s, 3H); EIMS m/z 331.

Example 7

Preparation of methyl 4,6-dichloro-3-vinylpicolinate

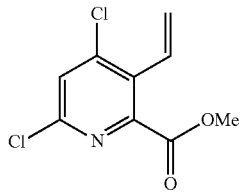

Methyl 4,6-dichloro-3-iodopicolinate (0.56 g, 1.7 mmol), vinyltributylstannane (580 μl, 0.63 g, 2.0 mmol) and bis(triphenylphosphine)palladium(II) chloride (0.12 g, 0.17 mmol) were combined in 1,2-dichloroethane (8 mL) and the mixture was sparged with a stream of nitrogen for 15 min. The reaction mixture was stirred at reflux for 21 h, cooled to room temperature, and diluted with ethyl acetate (15 mL). A solution of 20% KHF$_2$ (10 ml) was added and the mixture was stirred for 45 minutes. The mixture was filtered through Celite. The organic phase was washed with water, washed with saturated sodium chloride, dried over sodium sulfate, and concentrated under vacuum. The crude product was purified by flash chromatography (SiO$_2$, ethyl acetate/hexanes) to afford the title compound as a solid (0.30 g, 70%): $^1$H NMR (400 MHz, CDCl$_3$) δ 7.50 (s, 1H), 6.82 (ddd, J=17.8, 11.5, 1.7 Hz, 1H), 5.66 (dd, J=11.4, 8.1 Hz, 1H), 5.55 (dt, J=17.7, 5.0 Hz, 1H), 3.92 (s, 3H); EIMS m/z 231.

Example 8

Preparation of methyl 4-amino-6-chloro-3-vinylpicolinate (Compound 3)

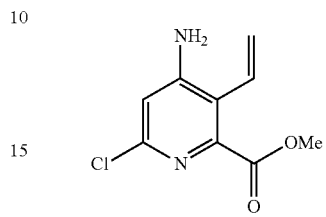

Methyl 4,6-dichloro-3-vinylpicolinate (0.25 g, 1.1 mmol) and sodium azide (0.19 g, 3 mmol) were combined in dry dimethylformamide (4 mL) and heated at 60° C. for 5 h. The mixture was cooled and then stirred at room temperature for 18 h. Ethyl acetate and water were added to the mixture and the aqueous phase was extracted with ethyl acetate. The combined organics were washed with water, washed with saturated sodium chloride, dried over sodium sulfate, and concentrated under vacuum. The crude product was purified by flash chromatography (SiO$_2$, ethyl acetate/hexanes) to afford the azide. The azide was dissolved in anhydrous methanol (5 mL) and treated with sodium borohydride (30 mg, 0.75 mmol) and the reaction mixture was stirred for 30 minutes. Water and ethyl acetate were added to the reaction mixture and it was stirred for 15 minutes. The organic phase was concentrated under vacuum and the crude product was purified by flash chromatography (SiO$_2$, methylene chloride, followed by ethyl acetate/hexanes) to afford the title compound as a tan solid (0.10 g, 43%): mp 53-54° C.; $^1$H NMR (400 MHz, CDCl$_3$) δ 6.78 (dd, J=18.1, 11.5 Hz, 1H), 6.68 (s, 1H), 5.65 (dd, J=11.5, 1.4 Hz, 1H), 5.49 (dd, J=18.1, 1.4 Hz, 1H), 4.80 (s, 2H), 3.88 (s, 3H); EIMS m/z 212 [(M−H)$^−$].

Example 9

Preparation of propan-2-yl 4,5,6-trichloropicolinate

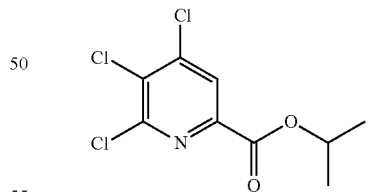

Methyl 4,5,6-trichloropicolinate (prepared as in Balko, T. W. et al. U.S. Pat. No. 6,784,137 B2, Aug. 31, 2004; 14.19 g, 59.0 mmol) was slurried in 2-propanol (150 mL) in a 250 mL round bottom flask equipped with a Dean-Stark trap and a reflux condenser. Sulfuric acid (98% H$_2$SO$_4$; 8.07 g, 82 mmol) was added, and the reaction mixture was heated to reflux. After 20 h at reflux, the majority of the 2-propanol (100 mL) was distilled overhead. The remaining reaction mixture solidified upon cooling to room temperature. The resulting solid was stirred with EtOAc (500 mL) and satd aq NaHCO$_3$ (500 mL). The organic layer was separated, washed with satd aq NaCl, and then filtered through Celite. The organic extract was concentrated to 150 mL by rotary evaporation. Hexane (100 mL) was added, and the solution was stored at −20° C. overnight. Crystals were collected, washed with hexane and dried in air (7.58 g, mp 104.6-105.7° C.). A second crop was obtained by concentration of the filtrate to give a total of 10.36 g (65%): $^1$H NMR (400 MHz, DMSO-$d_6$) δ 8.23 (s, 1H, pyridine H), 5.16 (septet, J=6.3 Hz, 1H, CHMe$_2$), 1.34 (d, J=6.3 Hz, 6H, CHMe$_2$); $^{13}$C{$^1$H} NMR (101 MHz, CDCl$_3$) δ 161.9 (CO$_2$R), 150.6, 145.9, 145.0, 133.1, 125.4 (C3), 70.7 (CHMe$_2$), 21.7 (Me). Anal. Calcd for C$_9$H$_8$Cl$_3$NO$_2$: C, 40.26; H, 3.00; N, 5.22. Found: C, 40.25; H, 3.02; N, 5.22.

Example 10

Preparation of propan-2-yl 4,5,6-trifluoropicolinate

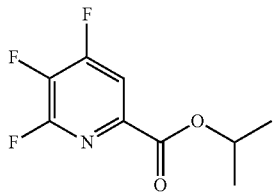

A 250 mL three-neck flask was equipped with a mechanical stirrer, a Dean-Stark trap with nitrogen inlet, and a thermocouple. The flask was purged with nitrogen and CsF (23.38 g, 154 mmol) was added. Anhydrous DMSO (124 mL) was added and the suspension was evacuated/backfilled (5×) with nitrogen. The suspension was heated at 80° C. for 30 min. DMSO (20 mL) was distilled off under vacuum at 75° C. to remove any residual water. Propan-2-yl 4,5,6-trichloropicolinate (13.45 g, 50.1 mmol) was added against a nitrogen purge. The reaction mixture was evacuated/backfilled (3×) and heated at 100° C. for 1 h with vigorous stirring.

A second 250 mL three-neck flask was equipped with a mechanical stirrer, a Dean-Stark trap with nitrogen inlet, and a thermocouple. The flask was purged with nitrogen and CsF (24.41 g, 0.160 mmol) was added. Anhydrous DMSO (30 mL) was added, and the suspension was evacuated/backfilled (5×) with nitrogen. The suspension was heated to 80° C. for 30 min. DMSO (22 mL) was distilled off under vacuum at 75° C. to remove residual water. The cooled reaction mixture in the first flask was cannula filtered into the second flask under nitrogen. The reaction mixture was evacuated/backfilled (5×) and then heated at 100° C. for 1 h and then for an additional 90 min at 110° C. Analysis of an aliquot by gas chromatography (GC) showed 96% propan-2-yl 4,5,6-trifluoropicolinate with only 1.4% propan-2-yl 5-chloro-4,6-difluoropicolinate present. The crude product solution was used directly in the amination step without further purification. Alternatively, the product can be isolated by aqueous workup, extraction with EtOAc, and drying to give a light tan oil: $^1$H NMR (400 MHz, CDCl$_3$) δ 7.94 (dd, J$_{F-H}$=4.5, 8.7 Hz, 1H, H3), 5.30 (septet, J$_{H-H}$=6.3 Hz, 1H, CHMe$_2$), 1.44 (d, J$_{H-H}$=6.3 Hz, 6H, CHMe$_2$); $^{13}$C {$^1$H} NMR (101 MHz, CDCl$_3$) δ 161.2 (s, CO$_2$iPr), 157.3 (ddd, J$_{F-C}$=266, 8, 6 Hz, C4/C6), 152.2 (ddd, J$_{F-C}$=241, 12, 5 Hz, C4/C6), 141.1 (dt, J$_{F-C}$=14, 7 Hz, C2), 137.0 (ddd, J$_{F-C}$=270, 31, 13 Hz, C5), 113.8 (dd, J$_{F-C}$=17, 4 Hz, C3), 70.4 (s, CHMe$_2$), 21.33 (s, Me); $^{19}$F NMR (376 MHz, CDCl$_3$) δ −74.29 (dd, J$_{F-F}$=24, 22 Hz, F6), −112.67 (ddd, J$_{F-F}$=22, 19, J$_{F-H}$=8.3 Hz, F4), −151.58 (ddd, J$_{F-F}$=24, 19, J$_{F-H}$=4.7 Hz, F5).

Example 11

Preparation of propan-2-yl 4-amino-5,6-trifluoropicolinate

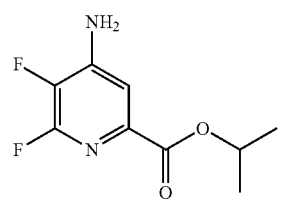

The reaction mixture from Example 21 was filtered to remove Cs salts, and the salts were washed with DMSO (50 mL). The DMSO washing solution was added to the DMSO solution (150 mL) which had been saturated with ammonia (NH$_3$) for 15 min. The flask was kept in a cold bath which kept the temperature near 16° C. NH$_3$ was bubbled through the reaction mixture for 30 min, during which time a white precipitate formed. After 90 min, analysis of an aliquot by GC showed a single major peak for the 4-amino product. The reaction mixture was quenched by addition of satd aq NR$_4$Cl (100 mL), followed by H$_2$O (400 mL). The aqueous solution was extracted into Et$_2$O (3×150 mL) and then EtOAc (3×150 mL). The combined organic extracts were washed with H$_2$O (5×150 mL) and then satd aq NaCl. The extracts were dried (MgSO$_4$) and evaporated to a tan solid, which was washed with 1:1 hexane-Et$_2$O to give a light tan powder (5.57 g, 51.4% overall): mp 168-170° C.; $^1$H NMR (400 MHz, CDCl$_3$) δ 7.42 (d, J$_{F-H}$=5.5 Hz, 1H, pyridine H), 5.22 (septet, J=6.2 Hz, 1H, CHMe$_2$), 4.75 (s, 2H, NH$_2$), 1.35 (d, J=6.2 Hz, 6H, CHMe$_2$); $^{13}$C{$^1$H} NMR (101 MHz, DMSO-$d_6$) δ 162.8 (CO$_2$R), 151.2 (dd, J$_{F-C}$=228, 12 Hz, C6), 146.5 (dd, J$_{F-C}$=9, 6 Hz, C2/C4), 139.3 (dd, J$_{F-C}$=16, 5 Hz, C2/C4), 133.8 (dd, J$_{F-C}$=252, 31 Hz, C5), 112.3 (C3), 68.8 (CHMe$_2$), 21.5 (Me); $^{19}$F NMR (376 MHz, DMSO-$d_6$) δ −91.9 (d, J$_{F-F}$=26.6 Hz, F6), −163.9 (dd, J$_{F-F}$=26.6, J$_{H-F}$=5.6 Hz, F5). Anal. Calcd for C$_9$H$_{10}$F$_2$N$_2$O$_2$: 50.00; H, 4.66; N, 12.96. Found: C, 49.96; H, 4.65; N, 12.91.

Example 12

Preparation of propan-2-yl 4-amino-6-chloro-5-fluoropicolinate

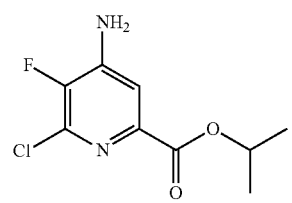

Propan-2-yl 4-amino-5,6-difluoropicolinate (4.25 g, 19.7 mmol) was dissolved in HCl (4 M in dioxane; 65 mL) in a 100 mL Hastalloy stirred Parr reactor. The reactor was heated at 100° C. for 2 h. Upon standing at room temperature overnight, a yellow crystalline solid formed. This solid was not soluble in EtOAc but did dissolve upon shaking with satd aq NaHCO$_3$ (500 mL) and EtOAc (300 mL). The aqueous layer was extracted with EtOAc (2×250 mL). The combined organic extracts were washed with H$_2$O (5×50 mL) and then with satd aq NaCl. The extracts were dried (MgSO$_4$) and concentrated under vacuum to provide an off-white solid. The crude product was purified by column chromatography (120 g silica column; 0-100% hexane-EtOAc gradient) to give a white solid (2.11 g, 46%): mp 190.7-192.4° C.; $^1$H NMR (400 MHz, DMSO-d$_6$) δ 7.543 (d, $J_{F-H}$=5.7 Hz, 1H), 6.91 (br s, 2H, NH$_2$), 5.09 (septet, J=6 Hz, 1H, CHMe$_2$), 1.29 (d, J=6 Hz, 6H, CHMe$_2$); $^{13}$C{$^1$H} NMR (101 MHz, DMSO-d$_6$) δ 162.8 (CO$_2$R), 144.8 (d, $J_{F-C}$=12 Hz, C2/C4), 143.4 (d, $J_{F-C}$=254 Hz, C5), 142.7 (d, $J_{F-C}$=4.8 Hz, C2/C4), 136.5 (d, $J_{F-C}$=17 Hz, C6), 112.8 (d, $J_{F-C}$=5 Hz, C3), 68.9 (CHMe$_2$), 21.6 (Me); $^{19}$F NMR (376 MHz, DMSO-d$_6$) δ -141.0 (d, $J_{F-H}$=6 Hz). Anal. Calcd for C$_9$H$_{10}$ClFN$_2$O$_2$: C, 46.47; H, 4.33; N, 13.75. Found: C, 46.50; H, 4.33; N, 11.96.

Example 13

Preparation of methyl 4-amino-6-chloro-5-fluoropicolinate

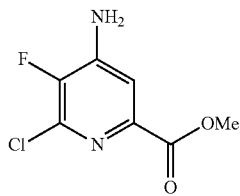 [SMILES: COC(=O)c1cc(N)c(F)c(Cl)n1]

Isopropyl 4-amino-6-chloro-5-fluoropicolinate (1.35 g, 5.80 mmol) was dissolved in anhydrous CH$_3$OH (50 mL), treated with titanium(IV) isopropoxide (300 mg, 2.2 mmol), and heated at reflux for 4 h. After cooling, the volatiles were removed under vacuum, and the residue was taken up in EtOAc (30 mL). This solution was stirred with H$_2$O (1 mL) for 20 min and then filtered through diatomaceous earth. The filtrate was washed with satd aq NaCl (10 mL), dried (Na$_2$SO$_4$), and evaporated to give the title compound (1.2 g, 97%): mp 180-183° C.; $^1$H NMR (400 MHz, DMSO-d$_6$) δ 7.45 (d, J=6.0 Hz, 1H), 6.93 (s, 2H), 3.83 (s, 3H); $^{19}$F NMR (376 MHz, DMSO-d$_6$) δ -131.36, -131.42, -135.47, -135.53; EIMS m/z 204.

Example 14

Preparation of methyl 4-amino-6-chloro-5-fluoro-3-iodopicolinate

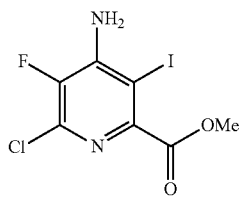 [SMILES: COC(=O)c1nc(Cl)c(F)c(N)c1I]

Methyl 4-amino-6-chloro-5-fluoropicolinate (2.2 g, 10.8 mmol) was dissolved in methyl alcohol (20 mL). The solution was treated with periodic acid (880 mg, 3.9 mmol) and iodine (2.2 g, 8.6 mmol) and then heated at reflux for 20 h. The mixture was cooled, and the volatiles were removed under vacuum. The residue was dissolved in EtOAc (50 mL) and then stirred with 10% NaHSO$_3$ solution (20 mL) for 10 min. The organic phase was separated and washed with satd aq NaCl (10 mL), dried (Na$_2$SO$_4$) and evaporated. The residue was purified by silica gel chromatography (5-50% EtOAc-hexane gradient) to give the title compound as a light orange solid (2.5 g, 70%): mp 149-151° C.; ESIMS m/z 330 ([M]$^+$); $^1$H NMR (400 MHz, CDCl$_3$) δ 5.17 (s, 2H, NH$_2$), 3.97 (s, 3H, OMe); $^{19}$F NMR (376 MHz, CDCl$_3$) δ -135.79 (s).

Example 15

Preparation of (Z)-methyl 4-amino-6-chloro-5-fluoro-3-(prop-1-en-1-yl)picolinate (Compound 4)

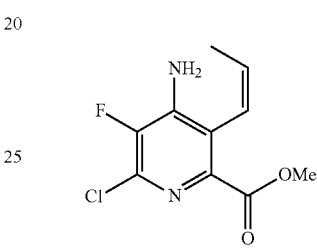

Methyl 4-amino-6-chloro-5-fluoro-3-iodopicolinate (0.4 g, 1.210 mmol), (E)-tributyl(prop-1-en-1-yl)stannane (0.481 g, 1.452 mmol), and bis(triphenylphosphine)palladium(II) chloride (0.085 g, 0.121 mmol) in dichloroethane (2.42 mL) were irradiated at 120° C. for 30 min in a microwave reactor. Celite was then added to the reaction mixture and the solvent was removed under vacuum. The crude product was first purified by flash column chromatography (SiO$_2$, hexane/EtOAc gradient) then by reverse phase HPLC to afford the title compound as an orange oil: $^1$H NMR (400 MHz, CDCl$_3$) δ 6.39 (dq, J=11.1, 1.7 Hz, 1H), 6.07 (dq, J=11.2, 6.9 Hz, 1H), 4.64 (s, 2H), 3.89 (s, 3H), 1.55 (dd, J=6.9, 1.7 Hz, 3H); $^{19}$F NMR (376 MHz, CDCl$_3$) δ -139.48; EIMS m/z 245 ([M+H]$^+$).

Compound 5 in Table 1 was synthesized as in Example 15 (Note: The reaction conditions described in Example 15 led to the formation of both the E and Z isomers with the (E)-tributyl (prop-1-en-1-yl) stannane starting material.

Example 16

Preparation of methyl 4-amino-6-chloro-5-fluoro-3-(1-fluorovinyl)picolinate (Compound 6)

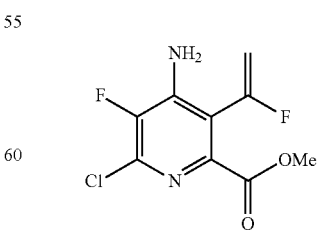

Methyl 4-amino-6-chloro-5-fluoro-3-iodopicolinate (0.4 g, 1.210 mmol), tributyl(1-fluorovinyl)stannane (0.608 g, 1.816 mmol), and bis(triphenyl-phosphine)palladium(II)

chloride (0.127 g, 0.182 mmol) were combined in dichloroethane (2.4 mL) and stirred at 70° C. overnight. The reaction mixture was concentrated onto celite and purified by flash column chromatography (SiO₂, hexanes/EtOAc gradient) to afford the title compound (211 mg, 0.849 mmol, 70.1% yield) as a yellow solid: mp 98-100° C.; $^1$H NMR (400 MHz, CDCl₃) δ 5.28 (dd, J=15.0, 3.6 Hz, 1H), 4.94 (s, 2H), 4.81 (dd, J=47.3, 3.6 Hz, 1H), 3.93 (s, 3H); $^{19}$F NMR (376 MHz, CDCl₃) δ −89.04, −138.74; ESIMS m/z 249 [(M+H)⁺].

Example 17

Preparation of (E)-methyl 4-amino-6-chloro-5-fluoro-3-(2-(trimethylsilyl)vinyl)picolinate (Compound 7)

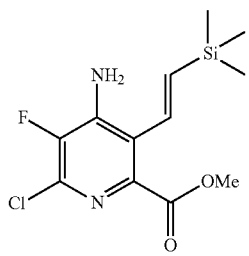 [SMILES: COC(=O)c1nc(Cl)c(F)c(N)c1/C=C/[Si](C)(C)C]

Methyl 4-amino-6-chloro-5-fluoro-3-iodopicolinate (0.5 g, 1.513 mmol), (E)-trimethyl(2-(tributylstannyl)vinyl)silane (0.589 g, 1.513 mmol), and bis(triphenylphosphine)palladium(II) chloride (0.106 g, 0.151 mmol) were combined in dichloroethane (3 mL) and stirred at 70° C. overnight. The reaction mixture was concentrated onto celite then purified by flash chromatography (SiO₂, hexanes/EtOAc gradient) to afford the title compound (285 mg, 0.941 mmol, 62.2% yield) as an orange solid: mp 103-105° C.; $^1$H NMR (400 MHz, CDCl₃) δ 6.99 (d, J=19.8 Hz, 1H), 6.21 (d, J=19.9 Hz, 1H), 4.72 (s, 2H), 3.89 (s, 3H), 0.19 (s, 9H); $^{19}$F NMR (376 MHz, CDCl₃) δ −139.10; ESIMS m/z 301 [(M−H)⁻].

Example 18

Preparation of (E)-methyl 4-amino-6-chloro-3-(2-chlorovinyl)-5-fluoropicolinate (Compound 8)

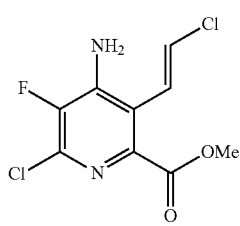 [SMILES: COC(=O)c1nc(Cl)c(F)c(N)c1/C=C/Cl]

To a solution of (E)-methyl 4-amino-6-chloro-5-fluoro-3-(2-(trimethylsilyl)vinyl)picolinate (176 mg, 0.581 mmol) in DMF (2.3 mL) was added N-chlorosuccinimide (116 mg, 0.872 mmol). The reaction mixture was stirred at 60° C. After 4 h, the observed conversion was ~50%. At this point, the reaction mixture was poured into water (30 mL) and extracted with EtOAc (3×). The combined organic layers were dried over Na₂SO₄, filtered, and concentrated. The crude product was purified by flash column chromatography (SiO₂, hexane/EtOAc gradient) to afford the title compound (75 mg, 0.283 mmol, 48.7% yield) as an orange solid: mp 128-130° C.; $^1$H NMR (400 MHz, CDCl₃) δ 6.97 (d, J=14.1 Hz, 1H), 6.45 (d, J=14.1 Hz, 1H), 4.73 (s, 2H), 3.93 (s, 3H); $^{19}$F NMR (376 MHz, CDCl₃) δ −138.17; ESIMS m/z 265 ([M]⁺).

Example 19

Preparation of 4-amino-6-chloro-5-fluoro-3-vinylpicolinic acid (Compound 9)

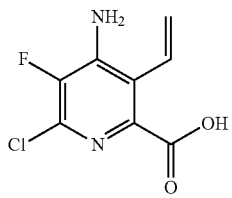

To a solution of methyl 4-amino-6-chloro-5-fluoro-3-vinylpicolinate (0.150 g, 0.650 mmol) in methanol (3.25 mL) and acetone (3.25 mL) was added sodium hydroxide (0.078 g, 1.951 mmol). The reaction mixture was stirred at room temperature overnight. The mixture was concentrated, diluted with ethyl acetate, and washed with 1N HCl. The organic phase was dried over Na₂SO₄, filtered, concentrated, and dried under high vacuum to afford the title compound (89 mg, 0.411 mmol, 63.2% yield) as a white solid: mp 164-166° C.; $^1$H NMR (400 MHz, DMSO) δ 13.34 (s, 1H), 6.67 (s, 2H), 6.67 (dd, J=17.7, 11.5 Hz, 3H), 5.53 (dd, J=10.4, 1.2 Hz, 1H), 5.49 (dd, J=16.7, 1.1 Hz, 1H); $^{19}$F NMR (376 MHz, DMSO) δ −142.00 (s); ESIMS m/z 215 ([M−H]⁻).

Compounds 10, 11, 12, 13, 14, 15, 16 in Table 1 were synthesized as in Example 19.

TABLE 1

| Compound No. | Name | Structure |
|---|---|---|
| 1 | methyl 4-amino-5,6-dichloro-3-vinylpicolinate | 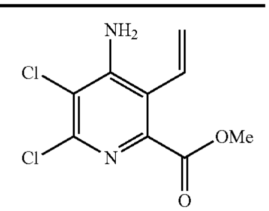 |
| 2 | methyl 4-amino-6-chloro-5-fluoro-3-vinylpyridine-2-carboxylate | 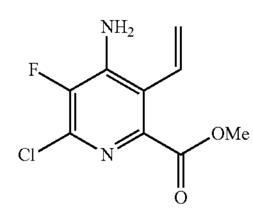 |

TABLE 1-continued

Compound Number, Name and Structure

| Compound No. | Name | Structure |
|---|---|---|
| 3 | methyl 4-amino-6-chloro-3-vinylpicolinate | 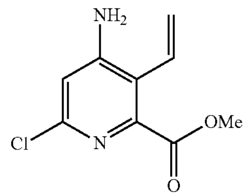 |
| 4 | (Z)-methyl 4-amino-6-chloro-5-fluoro-3-(prop-1-en-1-yl)picolinate | 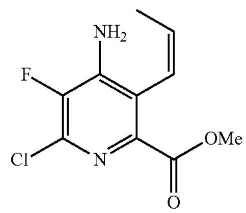 [SMILES: C/C=C\c1c(C(=O)OC)nc(Cl)c(F)c1N] |
| 5 | (E)-methyl 4-amino-6-chloro-5-fluoro-3-(prop-1-en-1-yl)picolinate | 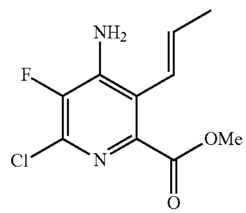 [SMILES: C/C=C/c1c(C(=O)OC)nc(Cl)c(F)c1N] |
| 6 | methyl 4-amino-6-chloro-5-fluoro-3-(1-fluorovinyl)picolinate | 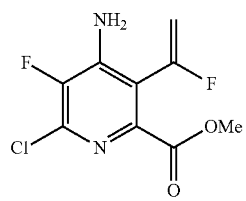 [SMILES: C=C(F)c1c(C(=O)OC)nc(Cl)c(F)c1N] |
| 7 | (E)-methyl 4-amino-6-chloro-5-fluoro-3-(2-(trimethylsilyl)vinyl)picolinate | 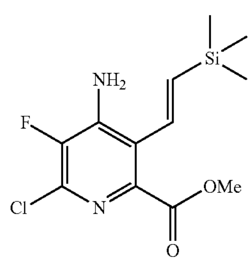 [SMILES: COC(=O)c1nc(Cl)c(F)c(N)c1/C=C/[Si](C)(C)C] |
| 8 | (E)-methyl 4-amino-6-chloro-3-(2-chlorovinyl)-5-fluoropicolinate | 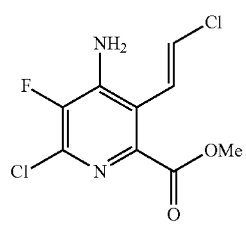 [SMILES: COC(=O)c1nc(Cl)c(F)c(N)c1/C=C/Cl] |
| 9 | 4-amino-6-chloro-5-fluoro-3-vinylpicolinic acid | 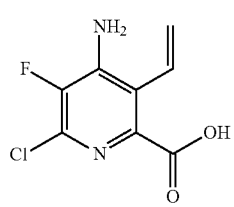 |
| 10 | 4-amino-5,6-dichloro-3-vinylpicolinic acid | 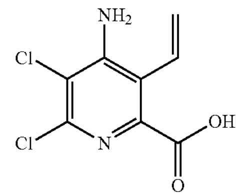 |
| 11 | 4-amino-6-chloro-3-vinylpicolinic acid | 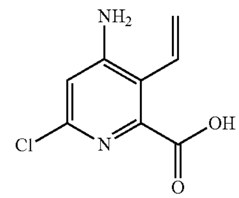 |
| 12 | (Z)-4-amino-6-chloro-5-fluoro-3-(prop-1-en-1-yl)picolinic acid | 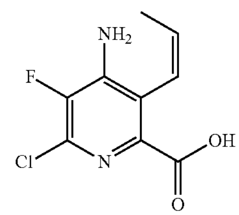 |
| 13 | (E)-4-amino-6-chloro-5-fluoro-3-(prop-1-en-1-yl)picolinic acid | 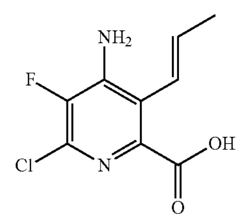 |
| 14 | 4-amino-6-chloro-5-fluoro-3-(1-fluorovinyl)picolinic acid | 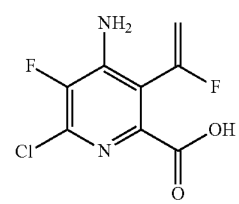 |
| 15 | (E)-4-amino-6-chloro-5-fluoro-3-(2-(trimethylsilyl)vinyl)picolinic acid | 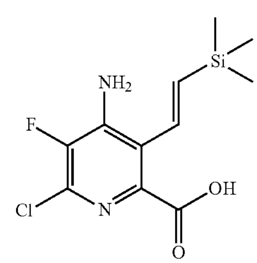 [SMILES: C[Si](C)(C)/C=C/c1c(C(=O)O)nc(Cl)c(F)c1N] |

TABLE 1-continued

Compound Number, Name and Structure

| Compound No. | Name | Structure |
|---|---|---|
| 16 | (E)-4-amino-6-chloro-3-(2-chlorovinyl)-5-fluoropicolinic acid | 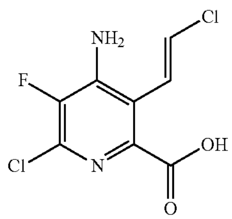 [SMILES: Nc1c(F)c(Cl)nc(C(=O)O)c1/C=C/Cl] |

TABLE 2

Compound Analytical Data

| Compound No. | Appearance | MP (°C.) | Mass | NMR |
|---|---|---|---|---|
| 1 | Tan Solid | 96-97 | EIMS m/z 246 ([M − H]⁻) | ¹H NMR (400 MHz, CDCl₃) δ 6.85 (dd, J = 18.1, 11.5 Hz, 1H), 5.72 (dd, J = 11.5, 1.3 Hz, 1H), 5.53 (dd, J = 18.1, 1.3 Hz, 1H), 5.19 (s, 2H), 3.91 (s, 3H). |
| 2 | light brown solid | 99-100 | EIMS m/z 230 ([M − H]⁻). | ¹H NMR (400 MHz, CDCl₃) δ 6.87 (dd, J = 18.1, 11.6 Hz, 1H), 5.72 (dd, J = 11.5, 1.3 Hz, 1H), 5.52 (dd, J = 18.2, 1.3 Hz, 1H), 4.79 (s, 2H), 3.91 (s, 3H). |
| 3 | Tan Solid | 53-54 | EIMS m/z 212 ([M − H]⁻) | ¹H NMR (400 MHz, CDCl₃) δ 6.78 (dd, J = 18.1, 11.5 Hz, 1H), 6.69 (s, 1H), 5.65 (dd, J = 11.5, 1.4 Hz, 1H), 5.49 (dd, J = 18.1, 1.4 Hz, 1H), 4.80 (s, 1H), 3.88 (s, 3H). |
| 4 | orange oil | | EIMS m/z 245 ([M + H]⁺) | ¹H NMR (400 MHz, CDCl₃) δ 6.39 (dq, J = 11.1, 1.7 Hz, 1H), 6.07 (dq, J = 11.2, 6.9 Hz, 1H), 4.64 (s, 2H), 3.89 (s, 3H), 1.55 (dd, J = 6.9, 1.7 Hz, 3H); ¹⁹F NMR (376 MHz, CDCl₃) δ −139.48 |
| 5 | white solid | 107-109 | EIMS m/z 245 ([M + H]⁺) | ¹H NMR (400 MHz, CDCl₃) δ 6.48 (dq, J = 16.3, 1.7 Hz, 1H), 5.96 (dq, J = 16.3, 6.6 Hz, 1H), 4.71 (s, 2H), 3.90 (s, 3H), 1.95 (dd, J = 6.6, 1.8 Hz, 3H); ¹⁹F NMR (376 MHz, CDCl₃) δ −139.33. |
| 6 | yellow solid | 98-100 | ESIMS m/z 249 [(M + H)⁺]. | ¹H NMR (400 MHz, CDCl₃) δ 5.28 (dd, J = 15.0, 3.6 Hz, 1H), 4.94 (s, 2H), 4.81 (dd, J = 47.3, 3.6 Hz, 1H), 3.93 (s, 3H); ¹⁹F NMR (376 MHz, CDCl₃) δ −89.04, −138.74 |
| 7 | orange solid | 103-105 | ESIMS m/z 301 [(M − H)⁻]. | ¹H NMR (400 MHz, CDCl₃) δ 6.99 (d, J = 19.8 Hz, 1H), 6.21 (d, J = 19.9 Hz, 1H), 4.72 (s, 2H), 3.89 (s, 3H), 0.19 (s, 9H); ¹⁹F NMR (376 MHz, CDCl₃) δ −139.10 |
| 8 | orange solid | 128-130 | ESIMS m/z 265 ([M]⁺). | ¹H NMR (400 MHz, CDCl₃) δ 6.97 (d, J = 14.1 Hz, 1H), 6.45 (d, J = 14.1 Hz, 1H), 4.73 (s, 2H), 3.93 (s, 3H); ¹⁹F NMR (376 MHz, CDCl₃) δ −138.17 |
| 9 | white solid | 164-166 | ESIMS m/z 215 ([M − H]⁻) | ¹H NMR (400 MHz, DMSO) δ 13.34 (s, 1H), 6.67 (s, 2H), 6.67 (dd, J = 17.7, 11.5 Hz, 3H), 5.53 (dd, J = 10.4, 1.2 Hz, 1H), 5.49 (dd, J = 16.7, 1.1 Hz, 1H); ¹⁹F NMR (376 MHz, DMSO) δ −142.00 (s) |
| 10 | White Solid | 190-193 (dec) | ESIMS m/z 233 ([M + H]⁺), 231 ([M − H]⁻) | ¹H NMR (400 MHz, DMSO) δ 13.45 (s, 1H), 6.75 (s, 1H), 6.68 (dd, J = 17.6, 11.4 Hz, 1H), 5.51 (t, J = 13.9 Hz, 1H). |
| 11 | White solid | 146-148 | ESIMS m/z 197 ([M − H]⁻) | H NMR (400 MHz, Acetone) δ 10.64 (d, J = 738.2 Hz, 1H), 6.92 (dd, J = 18.1, 11.6 Hz, 1H), 6.89 (s, 1H), 6.14 (s, 1H), 5.60 (dd, J = 11.7, 1.4 Hz, 1H), 5.55 (dd, J = 18.1, 1.5 Hz, 1H). |
| 12 | yellow solid | 141-143 | ESIMS m/z 229 ([M − H]⁻) | ¹H NMR (400 MHz, DMSO) δ 13.08 (s, 1H), 6.41 (s, 2H), 6.19 (dq, J = 11.1, 1.6 Hz, 1H), 5.92 (dq, J = 11.2, 6.9 Hz, 1H), 1.45 (dd, J = 6.9, 1.7 Hz, 3H); ¹⁹F NMR (376 MHz, DMSO) δ −141.36. |
| 13 | yellow solid | 153-155 | ESIMS m/z 229 ([M − H]⁻) | ¹H NMR (400 MHz, DMSO) δ 13.22 (s, 1H), 6.59 (s, 2H), 6.31 (dd, J = 16.0, 1.8 Hz, 1H), 5.89 (dq, J = 15.9, 6.5 Hz, 1H), 1.82 (dd, J = 6.5, 1.7 Hz, 3H); ¹⁹F NMR (376 MHz, DMSO) δ −142.26. |
| 14 | light brown solid | | | ¹H NMR (400 MHz, DMSO) δ 13.46 (s, 1H), 6.95 (s, 2H), 5.23 (dd, J = 15.4, 3.7 Hz, 1H), 4.87 (dd, J = 49.2, 3.7 Hz, 1H); ¹³C NMR (101 MHz, DMSO) δ 165.83, 156.45, 153.93, |

TABLE 2-continued

Compound Analytical Data

| Compound No. | Appearance | MP (° C.) | Mass | NMR |
|---|---|---|---|---|
| 15 | light yellow solid | 100-105 | ESIMS m/z 287 ([M − H]⁻) | 146.27, 146.22, 143.74, 143.61, 141.23, 135.90, 135.74, 113.10, 113.06, 112.81, 112.77, 98.68, 98.48; $^{19}$F NMR (376 MHz, DMSO) δ −89.71, −139.78. $^{1}$H NMR (400 MHz, DMSO) δ 13.28 (s, 1H), 6.80 (d, J = 19.3 Hz, 1H), 6.65 (s, 2H), 6.18 (d, J = 19.3 Hz, 1H), 0.13 (s, 9H); $^{19}$F NMR (376 MHz, DMSO) δ −142.26. |
| 16 | light brown solid | 152-157 | ESIMS m/z 252 ([M + H]⁺) | $^{1}$H NMR (400 MHz, DMSO) δ 13.46 (s, 1H), 6.85 (d, J = 13.7 Hz, 1H), 6.83 (s, 2H), 6.60 (d, J = 13.7 Hz, 1H); $^{19}$F NMR (376 MHz, DMSO) δ −141.24. |

Preparation of Herbicidal Compositions

In the following illustrative compositions, parts and percentages are by weight.

Emulsifiable Concentrates

Formulation A

|  | WT % |
|---|---|
| Compound 1 | 26.2 |
| Polyglycol 26-3 | 5.2 |
| Nonionic emulsifier-(di-sec-butyl)-phenyl-poly(oxypropylene)block polymer with (oxyethylene). The polyoxyethelene content is about 12 moles. |  |
| Witconate P12-20 (Anionic emulsifier-calcium dodecylbenzene sulfonate-60 wt. % active) | 5.2 |
| Aromatic 100 (Xylene range aromatic solvent) | 63.4 |

Formulation B

|  | WT % |
|---|---|
| Compound 2 | 3.5 |
| Sunspray 11N (paraffin oil) | 40.0 |
| Polyglycol 26-3 | 19.0 |
| Oleic acid | 1.0 |
| Xylene range aromatic solvent | 36.5 |

Formulation C

|  | WT % |
|---|---|
| Compound 2 | 13.2 |
| Stepon C-65 | 25.7 |
| Ethomeen T/25 | 7.7 |
| Ethomeen T/15 | 18.0 |
| Xylene range aromatic solvent | 35.4 |

Formulation D

|  | WT % |
|---|---|
| Compound 1 | 30.0 |
| Agrimer Al-10LC (emulsifier) | 3.0 |
| N-methyl-2-pyrrolidone | 67.0 |

Formulation E

|  | WT % |
|---|---|
| Compound 2 | 10.0 |
| Agrimul 70-A (dispersant) | 2.0 |
| Amsul DMAP 60 (thickener) | 2.0 |
| Emulsogen M (emulsifier) | 8.0 |
| Attagel 50 (suspension aid) | 2.0 |
| Crop oil | 76.0 |

These concentrates can be diluted with water to give emulsions of suitable concentrations for controlling weeds.

Wettable Powders

Formulation F

|  | WT % |
|---|---|
| Compound 1 | 26.0 |
| Polyglycol 26-3 | 2.0 |
| Polyfon H | 4.0 |
| Zeosyl 100 (Precipitated hydrated SiO₂) | 17.0 |
| Barden clay + inerts | 51.0 |

Formulation G

|  | WT % |
|---|---|
| Compound 1 | 62.4 |
| Polyfon H (sodium salt of lignin sulfonate) | 6.0 |
| Sellogen HR (sodium naphthalene sulfonate) | 4.0 |
| Zeosyl 100 | 27.6 |

Formulation H

|  | WT % |
|---|---|
| Compound 3 | 1.4 |
| Kunigel V1 (carrier) | 30.0 |
| Stepanol ME Dry (wetter) | 2.0 |
| Tosnanon GR 31A (binder) | 2.0 |
| Kaolin NK-300 Clay (filler) | 64.6 |

The active ingredient is applied to the corresponding carriers and then these are mixed and ground to yield wettable powders of excellent wettability and suspension power. By diluting these wettable powders with water it is possible to obtain suspensions of suitable concentrations for controlling weeds.

Water Dispersible Granules
Formulation I

|  | WT % |
| --- | --- |
| Compound 3 | 26.0 |
| Sellogen HR | 4.0 |
| Polyfon H | 5.0 |
| Zeosyl 100 | 17.0 |
| Kaolinite clay | 48.0 |

The active ingredient is added to the hydrated silica, which is then mixed with the other ingredients and ground to a powder. The powder is agglomerated with water and sieved to provide granules in the range of −10 to +60 mesh. By dispersing these granules in water it is possible to obtain suspensions of suitable concentrations for controlling weeds.

Granules
Formulation J

|  | WT % |
| --- | --- |
| Compound 2 | 5.0 |
| Celetom MP-88 | 95.0 |

The active ingredient is applied in a polar solvent such as N-methylpyrollidinone, cyclohexanone, gamma-butyrolactone, etc. to the Celetom MP 88 carrier or to other suitable carriers. The resulting granules can be applied by hand, granule applicator, airplane, etc. in order to control weeds.

Formulation K

|  | WT % |
| --- | --- |
| Compound 3 | 1.0 |
| Polyfon H | 8.0 |
| Nekal BA 77 | 2.0 |
| Zinc Stearate | 2.0 |
| Barden Clay | 87.0 |

All materials are blended and ground to a powder then water is added and the clay mixture is stirred until a paste is formed. The mixture is extruded through a die to provide granules of proper size.

Water Soluble Liquids
Formulation L

|  | WT % |
| --- | --- |
| Compound 3 | 3.67 |
| Monoethanolamine pH buffer | 0.5 |
| Water | 95.83 |

The active ingredient is dissolved in an appropriate amount of water and the additional monoethanolamine is added as a buffer. A water-soluble surfactant may be added. Other aids may be incorporated to improve physical, chemical and/or formulation properties.

Evaluation of Postemergence Herbicidal Activity

Seeds or nutlets of the desired test plant species were planted in Sun Gro MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7-21 days in a greenhouse with an approximate 15 hour photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was placed in a 25 mL glass vial and was dissolved in 4 mL of a 97:3 v/v (volume/volume) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton® X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 (v/v) mixture of acetone and dimethyl sulfoxide (DMSO) and 10 mL of an aqueous mixture containing acetone, water, isopropyl alcohol, DMSO, Atplus 411F crop oil concentrate, and Triton X-155 surfactant in a 48.5:39:10:1.5:1.0:0.02 (v/v) ratio to obtain ½X, ¼X, ⅛X and 1/16X rates of the high rate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 square meters at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 days, the condition of the test plants as compared with that of the untreated plants was determined visually and scored on a scale of 0 to 100 percent where 0 corresponds to no injury and 100 corresponds to complete kill By applying the well-accepted probit analysis as described by J. Berkson in *Journal of the American Statistical Society*, 48, 565 (1953) and by D. Finney in "*Probit Analysis*" Cambridge University Press (1952), the above data can be used to calculate $GR_{50}$ and $GR_{80}$ values, which are defined as growth reduction factors that correspond to the effective dose of herbicide required to kill or control 50 percent or 80 percent, respectively, of a target plant.

Some of the compounds tested, application rates employed, plant species tested, and results are given in Table 3.

TABLE 3

| Post-emergent control of weeds. | | | | | | |
| --- | --- | --- | --- | --- | --- | --- |
|  | Rate | % Control | | | | |
| Compound # | (g ai/ha) | TRZAS | CHEAL | AMARE | CIRAR | POLCO |
| 1 | 280 | 0 | 100 | 100 | 95 | 100 |
| 2 | 140 | 55 | 90 | 100 | 70 | NT[1] |

TABLE 3-continued

Post-emergent control of weeds.

| | Rate | % Control | | | | |
|---|---|---|---|---|---|---|
| Compound # | (g ai/ha) | TRZAS | CHEAL | AMARE | CIRAR | POLCO |
| 3 | 280 | 20 | 100 | 100 | 100 | 100 |
| 4 | 140 | 0 | 100 | 100 | 85 | 40 |
| 5 | 140 | 0 | 90 | 0 | 65 | 20 |
| 6 | 140 | 0 | 90 | 20 | 75 | 90 |
| 7 | 140 | 0 | 100 | 90 | 55 | 50 |
| 8 | 140 | 0 | 90 | 90 | 70 | 60 |
| 9 | 140 | 50 | 100 | 100 | 100 | NT[1] |
| 10 | 280 | 20 | 100 | 100 | 100 | NT |
| 11 | 280 | 50 | 100 | NT | 10 | NT |
| 12 | 140 | 10 | 100 | 100 | 80 | 85 |
| 13 | 140 | 30 | 85 | 60 | 70 | 60 |
| 14 | 140 | 0 | 90 | 50 | 100 | 90 |
| 15 | 140 | 0 | 80 | NT | 65 | NT |
| 16 | 140 | 80 | 100 | 90 | 75 | 10 |

[1]Not tested

TRZAS—*Triticum aestivum* (spring wheat)
CHEAL—*Chenopodium album* (lambsquarters)
AMARE—*Amaranthus retroflexus* (pigweed)
CIRAR—*Cirsium arvense* (canada thistle)
POLCO—*Polygonum convolvulus* (wild buckwheat)

The foregoing is illustrative of the present invention, and is not to be construed as limiting thereof. The invention is defined by the following claims, with equivalents of the claims to be included therein.

What is claimed is:

1. A compound of the Formula I:

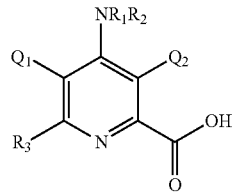

wherein
$Q_1$ is selected from the group consisting of hydrogen and halogen;
$Q_2$ is selected from the group consisting of $C_1$-$C_4$ alkenyl, $C_1$-$C_4$ haloalkenyl, and $CXCYSi(R_4)_3$;
X is selected from the group consisting of hydrogen, fluorine, and chlorine;
Y is selected from the group consisting of hydrogen, fluorine, chlorine, $C_1$-$C_4$ alkyl, and $C_1$-$C_4$ haloalkyl;
$R_1$ and $R_2$ are independently selected from the group consisting of hydrogen, $C_1$-$C_6$ alkyl, $C_3$-$C_6$ alkenyl, $C_3$-$C_6$ alkynyl, hydroxy, $C_1$-$C_6$ alkoxy, amino, $C_1$-$C_6$ acyl, $C_1$-$C_6$ carboalkoxy, $C_1$-$C_6$ alkylcarbamyl, $C_1$-$C_6$ alkylsulfonyl, $C_1$-$C_6$ trialkylsilyl, and $C_1$-$C_6$ dialkyl phosphonyl;
$R_3$ is selected from the group consisting of fluorine, chlorine, bromine, and iodine; and
$R_4$ is selected from the group consisting of $C_1$-$C_{10}$ alkyl, $C_3$-$C_6$ cycloalkyl, $C_1$-$C_{10}$ haloalkyl, $C_3$-$C_6$ halocycloalkyl, substituted or unsubstituted phenyl, $C_1$-$C_{10}$ alkoxy, and hydroxy.

2. The compound of claim 1 further comprising an agriculturally acceptable derivative of the carboxylic acid group.

3. A mixture comprising the compound of claim 1 and an agriculturally acceptable adjuvant or carrier.

* * * * *